US011636951B2

(12) United States Patent
Neumann

(10) Patent No.: US 11,636,951 B2
(45) Date of Patent: Apr. 25, 2023

(54) SYSTEMS AND METHODS FOR GENERATING A GENOTYPIC CAUSAL MODEL OF A DISEASE STATE

(71) Applicant: Kenneth Neumann, Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 16/590,426

(22) Filed: Oct. 2, 2019

(65) Prior Publication Data

US 2021/0104330 A1   Apr. 8, 2021

(51) Int. Cl.
| | |
|---|---|
| *G16H 50/50* | (2018.01) |
| *G16B 50/30* | (2019.01) |
| *G16B 40/10* | (2019.01) |
| *G16B 5/20* | (2019.01) |
| *G16H 50/70* | (2018.01) |
| *G06N 20/10* | (2019.01) |
| *G06N 5/02* | (2006.01) |
| *G16B 40/20* | (2019.01) |
| *G06N 5/025* | (2023.01) |

(52) U.S. Cl.
CPC ............. *G16H 50/50* (2018.01); *G06N 5/025* (2013.01); *G06N 20/10* (2019.01); *G16B 5/20* (2019.02); *G16B 40/10* (2019.02); *G16B 40/20* (2019.02); *G16B 50/30* (2019.02); *G16H 50/70* (2018.01)

(58) Field of Classification Search
CPC ........ G16H 50/50; G16H 50/70; G06N 20/10; G06N 5/025; G16B 50/30; G16B 5/20; G16B 40/10; G16B 40/20

See application file for complete search history.

(56) References Cited

U.S. PATENT DOCUMENTS

| | | | |
|---|---|---|---|
| 8,170,805 | B2 | 5/2012 | Kishore et al. |
| 9,940,434 | B2 | 4/2018 | Kingsmore et al. |
| 2006/0173663 | A1 | 8/2006 | Langheier et al. |
| 2007/0166707 | A1 | 7/2007 | Schadt et al. |
| 2010/0145624 | A1 | 6/2010 | Kishore et al. |
| 2011/0098193 | A1 | 4/2011 | Kingsmore |
| 2014/0066320 | A1 | 3/2014 | Heckerman et al. |
| 2017/0286594 | A1 | 10/2017 | Reid et al. |

(Continued)

FOREIGN PATENT DOCUMENTS

| | | |
|---|---|---|
| CN | 101617227 A | 12/2009 |
| WO | 2013070634 | 5/2013 |

OTHER PUBLICATIONS

Goddard et al; "PCAN: Phenotype Consensus Analysis to Support Disease-Gene Association"; BMC Bioinformatics; Dec. 7, 2016; https://www.ncbi.nlm.nih.gov/pubmed/27923364.

(Continued)

*Primary Examiner* — Olivia M. Wise
*Assistant Examiner* — Kaitlyn L Minchella
(74) *Attorney, Agent, or Firm* — Caldwell Intellectual Property Law

(57) ABSTRACT

A system for generating a genotypic causal model of a disease state includes a computing device that generates a causal graph containing genotypic causal nodes and connected symptomatic causal nodes, which contains causal paths from gene combinations to symptomatic datums. Genotypic causal nodes and/or connected symptomatic causal nodes may be generated by feature learning algorithms from training data.

18 Claims, 8 Drawing Sheets

(56) References Cited

U.S. PATENT DOCUMENTS

2017/0351807 A1   12/2017   Shtir et al.
2019/0102511 A1   4/2019    Murray et al.

OTHER PUBLICATIONS

Kramer et al; "Leveraging Network Analytics to Infer Patient Syndrome and Identify Causal Genes in Rare Disease Cases"; https://www.ncbi.nlm.nih.gov/pmc/articles/PMC5558lS5/; Jul. 9, 2019.

SYSTEMS AND METHODS FOR GENERATING A GENOTYPIC CAUSAL MODEL OF A DISEASE STATE

FIELD OF THE INVENTION

The present invention generally relates to the field of artificial intelligence. In particular, the present invention is directed to systems and methods for generating a genotypic causal model of a disease state.

BACKGROUND

There is a large and ever-increasing quantity of available data relevant to human physiology. However, use of that data to discover root cause information relating to particular conditions remains an elusive goal. This is due at least in part to the sheer quantity of data, and the resulting combinatoric explosion in possible correlations. Genetic sequencing data represents a particularly challenging situation. There are increasingly large populations of gene sequences being recorded, but the size of the human genome, combined with the complexities of its interaction with human physiology, makes use of this information a daunting task.

SUMMARY OF THE DISCLOSURE

In an aspect, a system for generating a genotypic causal model of a disease state, includes a computing device configured to perform the steps of generating a causal graph containing a plurality of causal nodes, the plurality of causal nodes including a plurality of genotypic causal nodes and a plurality of symptomatic causal nodes, where generating the causal graph further includes identifying, using a first feature learning algorithm, in training data containing a plurality of pairs of genetic sequences and disease states, a plurality of gene combinations correlated with each disease state of a plurality of disease states identified in the plurality of pairs, generating the plurality of genotypic causal nodes, wherein each genotypic causal node includes a disease state and a gene combination correlated with the disease state, receiving a symptomatic training set including a plurality of data entries containing a plurality of symptoms and a plurality of disease states, wherein each data entry includes a disease state and at least a correlated symptom, generating, using a second feature learning algorithm, the plurality of symptomatic nodes, wherein each symptomatic node includes a disease state and at least a correlated symptom, and connecting the plurality of symptomatic nodes to the plurality of genotypic nodes by instantiating edges connecting disease states of symptomatic nodes to matching disease states of genotypic nodes, receiving a genetic sequence, wherein the genetic sequence further includes a series of genes identified in a nucleotide sequence of chromosomal nucleic acid of a human subject, receiving a first symptomatic datum, and identifying at least a path in the causal graph from inputs in the genetic sequence to outputs at the first symptomatic datum, wherein the at least a path contains at least a genetic node and at least a linked symptomatic node, and generating a causal model using the at least a genetic node and the at least a linked symptomatic node.

In another aspect, a method of generating a genotypic causal model of a disease state, the method includes generating, by a computing device, a causal graph containing a plurality of causal nodes, the plurality of causal nodes including a plurality of genotypic causal nodes and a plurality of symptomatic causal nodes, wherein generating the causal graph further includes identifying, using a first feature learning algorithm, in training data containing a plurality of pairs of genetic sequences and disease states, a plurality of gene combinations correlated with each disease state of a plurality of disease states identified in the plurality of pairs, generating the plurality of genotypic causal nodes, wherein each genotypic causal node includes a disease state and a gene combination correlated with the disease state, receiving a symptomatic training set including a plurality of data entries containing a plurality of symptoms and a plurality of disease states, wherein each data entry includes a disease state and at least a correlated symptom, generating, using a second feature learning algorithm, the plurality of symptomatic nodes, wherein each symptomatic node includes a disease state and at least a correlated symptom, and connecting the plurality of symptomatic nodes to the plurality of genotypic nodes by instantiating edges connecting disease states of symptomatic nodes to matching disease states of genotypic nodes. The method includes receiving, by the computing device, a genetic sequence, wherein the genetic sequence further comprises a series of genes identified in a nucleotide sequence of chromosomal nucleic acid of a human subject. The method includes receiving, by the computing device, a first symptomatic datum. The method includes identifying, by the computing device, at least a path in the causal graph from inputs in the genetic sequence to outputs at the first symptomatic datum, wherein the at least a path contains at least a genetic node and at least a linked symptomatic node. The method includes generating, by the computing device, a causal model using the at least a genetic node and the at least a linked symptomatic node.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Embodiments disclosed herein use feature learning algorithms to identify likely causal relationships between genetic data and disease states, as well as likely causal relationships between disease states and symptoms. Such relationships are organized into a graph where causal relationships are represented using paths through the graph. This may enable complex relationships between genetics, disease states, and symptoms that were previously hidden to be generated and utilized for diagnostic and/or analytical purposes in a computationally parsimonious manner.

Figure 1:
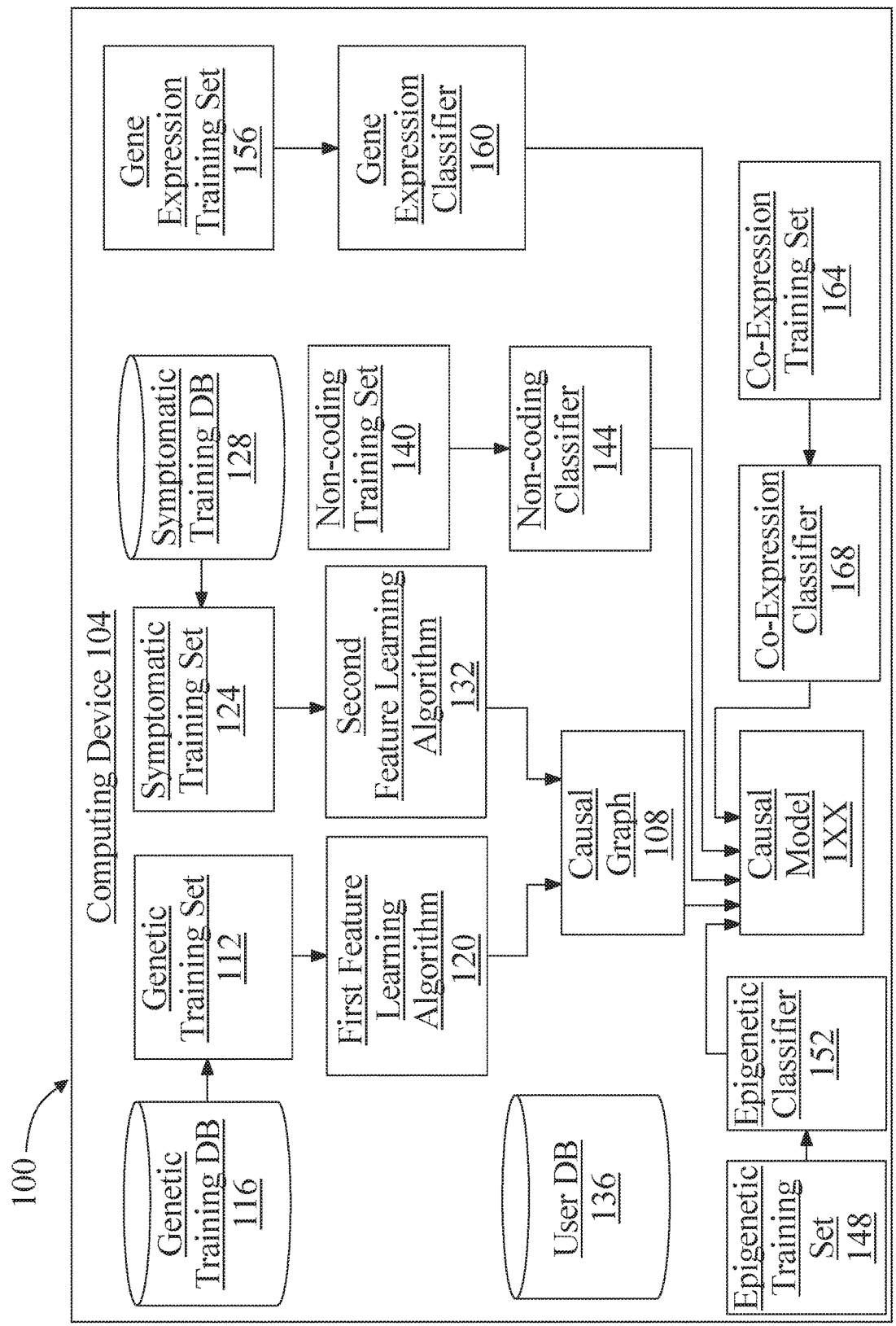
FIG. 1 is a block diagram illustrating an exemplary embodiment of a system for generating a genotypic causal model of a disease state.

Referring now FIG. 1 an exemplary embodiment of a system 100 for is illustrated. System 100 includes a computing device. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface and/or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. [computing device] may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

Still referring to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference, to FIG. 1, computing device is configured to generate a causal graph 108. As used herein, a "causal graph 108" is a directed graph representing causal chains from genes, through one or more disease states, to symptomatic data, where edges from one node to another represent causal links as established by machine learning processes as described in further detail below. A "disease state" as used in this disclosure is an abnormal condition that negatively affects the structure and/or function of part of a human body. A disease may include a current disease, such as a disease that may be diagnosed by a health professional who may be authorized by a particular health licensing board to diagnose disease and/or conditions such as for example a medical doctor, a doctor of osteopathy, a nurse practitioner, a physician assistant, a doctor of optometry, a doctor of dental medicine, a doctor of dental surgery, a naturopathic doctor, a doctor of physical therapy, a nurse, a doctor of chiropractic medicine, a doctor of oriental medicine, and the like; a disease state may include a disease that is causing a symptom as recorded in a symptomatic datum, as described in further detail below. A path through a causal graph 108 from genetic sequence data to symptomatic data may illustrate probable immediate disease state causes of symptomatic data, other disease states giving rise to the immediate disease state cause, well as probable genetic root causes and/or predispositions that represent genetic predispositions and/or mutations that cause and/or contribute to the disease state.

Figure 2:
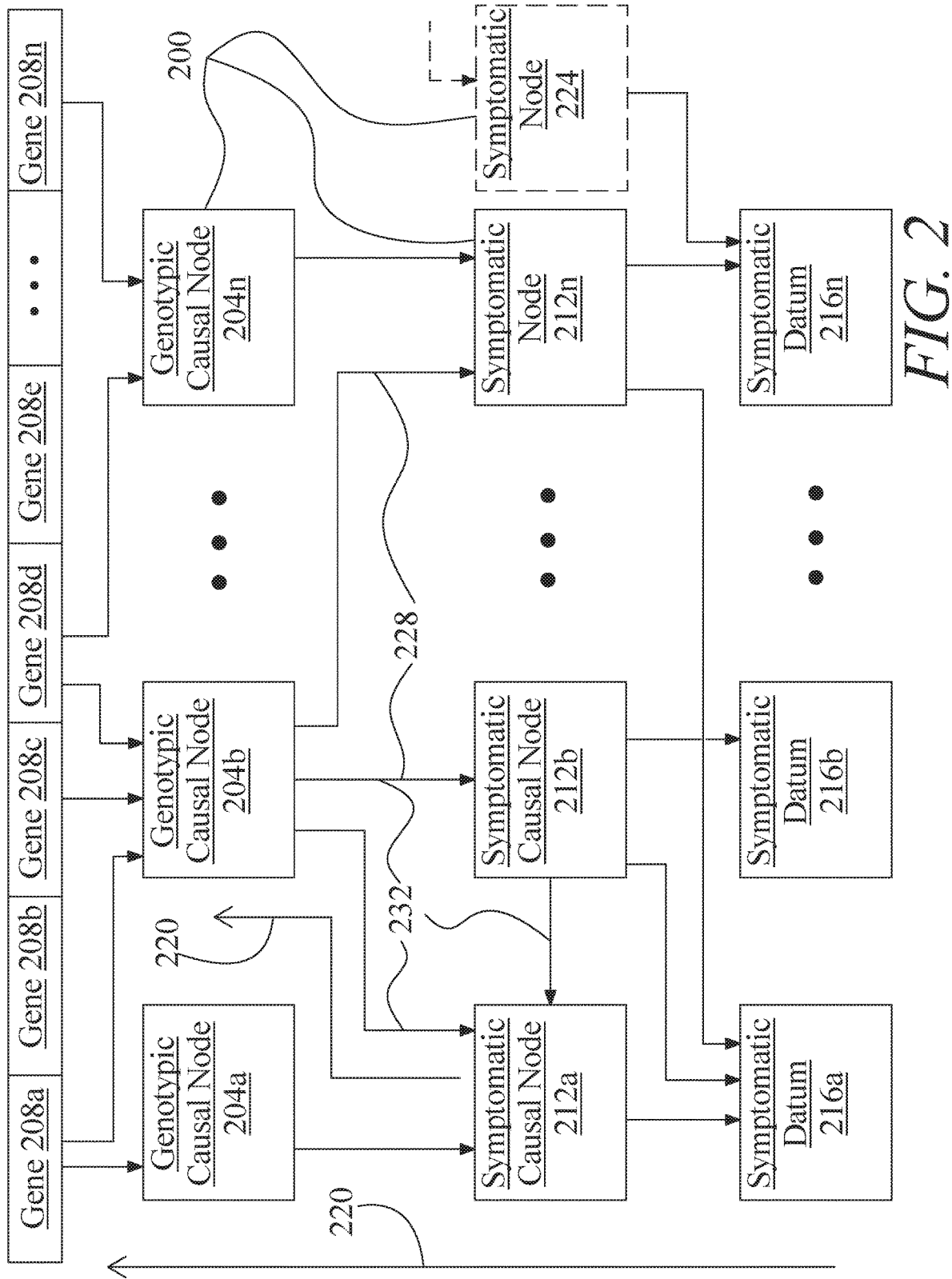
FIG. 2 is a block diagram illustrating an exemplary embodiment of a causal graph.

Referring now to FIG. 2, an exemplary embodiment of a causal graph 108 is illustrated. A causal graph 108 may include a plurality of causal nodes 200. A "causal node 200" as used in this disclosure is a data structure that links one or more effects, such as without limitation symptoms, disease states, test results, or the like, to one or more causes, such as underlying disease states and genes 208$a$-$n$. Linking to a cause may be performed by inclusion in a causal node 200 of at least a member or data element identifying a gene, a set of genes 208$a$-$n$, and/or another causal node 200 as representing a cause of a disease state represented by the causal node 200. Linking to an effect may be performed, without limitation, by inclusion in causal node 200 of an element of data identifying a symptom or other causal node 200 that is caused by a disease state represented in causal node 200. Linking to cause and/or linking to effect may alternatively or additionally be performed by a datum in another causal node 200 identifying a current causal node 200. Plurality of casual nodes may include a plurality of genotypic causal nodes 204a-n, where "genotypic causal nodes 204a-n" are nodes linking one or more genes 208a-n and/or combinations of genes 208a-n to a disease state. Plurality of causal nodes 200 may include a plurality of symptomatic causal nodes 212a-n, where "symptomatic causal nodes 212a-n" are nodes linking one or more disease states to one or more symptomatic datums 216a-n; a "symptomatic datum," as described herein, is an element of data describing one or more symptoms that a user is experiencing. A symptomatic datum may include an element of data describing any subjective description of a current or future probable disease that a user is experiencing. Subjective descriptions may include any phenomenon a user may be experiencing including for example anxiety, pain, fatigue, tremor, headache and the like. A symptomatic datum may be apparent as indicating a particular condition and/or disease such as when a user experiences blood loss from a subcutaneous flesh would. A symptomatic datum may not be apparent as indicating a particular condition and/or disease such as when a user may experience tiredness due to a thyroid disease which a user may believe is due to being overly fatigued. A symptomatic datum may be discovered using any form of diagnostic testing, including testing using a physically extracted sample such as a tissue sample, fluid sample, or the like, radiological testing, dexterity tests, or any other diagnostic tests and/or tests for physiological state data as described in U.S. Nonprovisional patent application Ser. No. 16/354,119, filed on Mar. 14, 2019, and entitled ARTIFICIAL INTELLIGENCE SYSTEMS AND METHODS FOR VIBRANT CONSTITUTIONAL GUIDANCE, the entirety of which is incorporated by reference herein.

Figure 5:
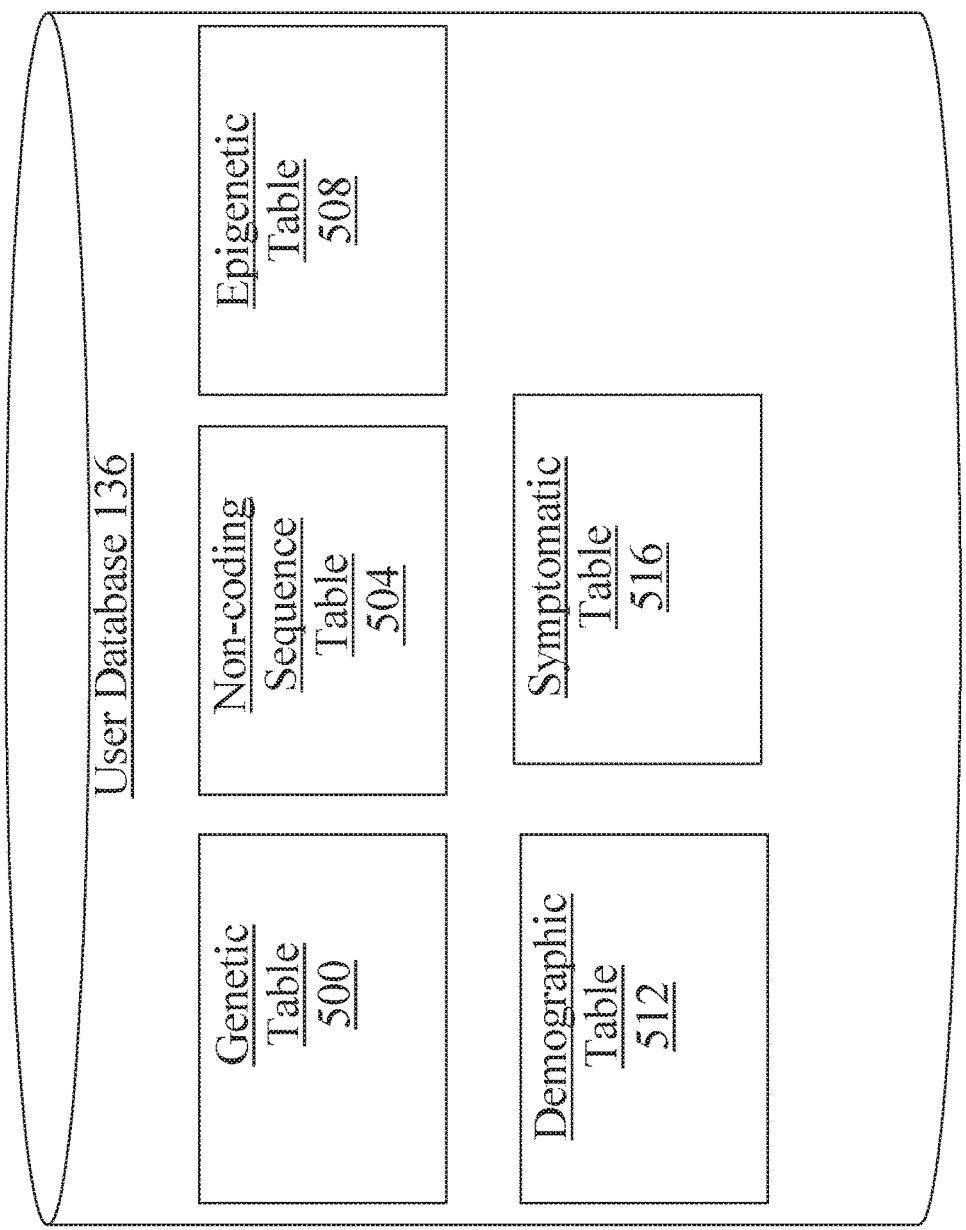
FIG. 5 is a block diagram illustrating an exemplary embodiment of a user database.

Still referring to FIG. 5, causal graph 108 may include one or more symptomatic causal nodes 212a-n that do not link to any genetic causal nodes 200; such nodes, referred to herein as "off graph nodes" may include an indicator that they have no apparent genetic cause, and/or that they have a purely non-genetic cause, as may, for instance, be the case with some infectious diseases such as influenza. In an embodiment, a path 220 leading "off graph" may be used as evidence that a symptomatic treatment approach is indicated, such as antibiotics for bacterial infections, anti-viral medication for viral infections, or the like. Alternatively or additionally, a medical professional may perform certain initial diagnostic steps to eliminate infectious agents or other non-genetically linked conditions prior to use of system 100 for diagnostic purposes.

Still referring to FIG. 2, computing device 104 may be configured to determine a path 220 through a causal graph 108 by finding a series of causal nodes 200 in the causal graph 108 connecting one or more genes 208a-n to a symptomatic datum. As a non-limiting example, computing device may use a symptomatic datum received from a user to determine one or more symptomatic nodes listing the symptomatic datum as an effect; the one or more symptomatic nodes may in turn be used to identify one or more earlier symptomatic nodes and/or one or more genotypic causal nodes 204a-n shown as causes for the one or more symptomatic nodes in the causal graph 108. Detection of causal nodes 200 causing a current symptomatic node may be repeated until arrival at genotypic causal nodes 204a-n, each of which may be used to identify a gene and/or cluster of genes 208a-n representing a cause for a chain of one or more causally linked disease states causing a symptomatic datum. As shown in FIG. 2, this may be effected by traversing a causal graph 108 from symptoms to genes 208a-n; alternatively or additionally, for instance where a single gene of a subject user is received, traversal may proceed from genes 208a-n to symptomatic datums 216a-n. Regardless of a starting point in causal graph 108, computing device 104 may detect more than one path 220 through causal graph 108.

Referring again to FIG. 1, computing device 104 may generate causal nodes 200 using one or more machine-learning processes. A machine learning process, also referred to as a machine-learning algorithm, is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language."

With continued reference to FIG. 1, training data, as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device may correlate any input data as described in this disclosure to any output data as described in this disclosure.

Continuing to refer to FIG. 1, machine-learning algorithms may be implemented using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure, Still referring to FIG. 1, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

With continued reference to FIG. 1, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

Still referring to FIG. 1, machine-learning algorithms may include supervised machine-learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised machine-learning process may include a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs.

With continued reference to FIG. 1, supervised machine-learning processes may include classification algorithms, defined as processes whereby a computing device derives, from training data, a model for sorting inputs into categories or bins of data. Classification may be performed using, without limitation, linear classifiers such as without limitation logistic regression and/or naive Bayes classifiers, nearest neighbor classifiers including without limitation k-nearest neighbors classifiers, support vector machines, decision trees, boosted trees, random forest classifiers, and/or neural network-based classifiers.

Still referring to FIG. 1, machine learning processes may include unsupervised processes. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like. Unsupervised machine-learning algorithms may include, without limitation, clustering algorithms and/or cluster analysis processes, such as without limitation hierarchical clustering, centroid clustering, distribution clustering, clustering using density models, subspace models, group models, graph-based models, signed graph models, neural models, or the like. Unsupervised learning may be performed by neural networks and/or deep learning protocols as described above.

Continuing to refer to FIG. 1, machine-learning processes as described in this disclosure may be used to generate machine-learning models. A machine-learning model, as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 1, computing device 104 is configured to generate a plurality of genotypic causal nodes 204a-n, wherein each genotypic causal node 204a-n includes a disease state and a gene combination correlated with the disease state. A "gene combination," as used in this disclosure, is a set of one or more genes 208a-n; thus, as a non-limiting example, a "gene combination" that may be correlated with a disease state may include a single gene correlated with the disease stated, such as the breast cancer (BRCA) gene associated with breast cancer, and/or particular forms of the HBB gene associated with sickle-cell disease. As a further non-limiting example, a gene combination may include two or more genes 208a-n associated with a health condition, including without limitation a potentially large number of genes 208a-n linked to an elevated risk of a given disease state. Some such correlations may be unknown in medical literature, for instance where a large number of different genes 208a-n in particular combinations may be linked to a given condition in ways that were not anticipated by existent hypotheses for potential causes of a condition. Computing device 104 may detect such novel combinations by performing one or more unsupervised machine-learning algorithms. In an embodiment, computing device identifies a gene combination correlated with a disease state in a genetic training set 112 containing a plurality of pairs of genetic sequences and disease states; such a training set may be compiled using genetic sequencing gathered from populations of patients suffering from diagnosed conditions, where genetic sequencing and/or diagnoses may be anonymized to protect patients' privacy. A pair of genetic sequence and disease state may include, for instance, a genetic sequence taken of a person who was diagnosed with a particular disorder, but for whom the diagnosis may not describe a genetic cause; latent patterns may be present in such data that, when considered in larger numbers, may make correlations between combinations of genes 208a-n and a given disease state apparent when analyzed.

With continued reference to FIG. 1, genetic training set 112 may be stored in and/or retrieved from a genetic training database 116. Genetic training database 116 may include any data structure for ordered storage and retrieval of data, which may be implemented as a hardware or software module. Genetic training database 116 may be implemented, without limitation, as a relational database, a key-value retrieval datastore such as a NOSQL database, or any other format or structure for use as a datastore that a person skilled in the art would recognize as suitable upon review of the entirety of this disclosure. Genetic training database 116 may include a plurality of data entries and/or records corresponding to user tests as described above. Data entries in a genetic training database 116 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a genetic training database 116 may reflect categories, cohorts, and/or populations of data consistently with this disclosure.

Figure 3:
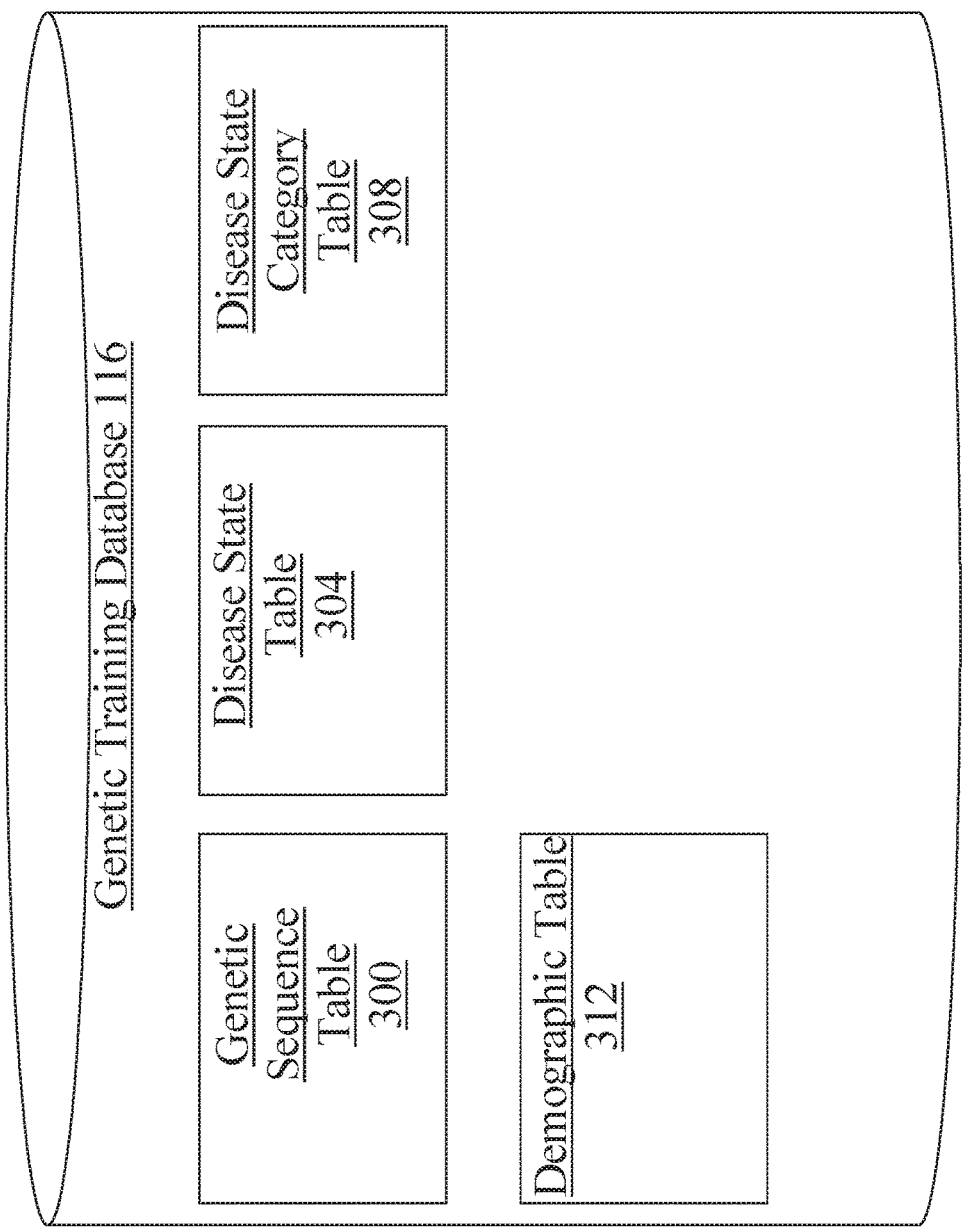
FIG. 3 is a block diagram illustrating an exemplary embodiment of a genetic training database.

Referring now to FIG. 3, an exemplary embodiment of a genetic training database 116 is illustrated. Genetic training database 116 may include one or more tables from which data records may be retrieved with linking data; linking data may include without limitation a genetic sequence index filed in which genetic sequence indices linking records from one or more tables to genetic sequences may be stored. As a non-limiting example, one or more tables may include a genetic sequence table 300 listing genetic sequences with genetic sequence indices. One or more tables may include a disease state table 304 listing one or more disease states that have been associated with a given genetic sequences disease states may be linked to genetic sequences using genetic sequence indices, which may indicate collection of disease state data corresponding to a person with regard to whom a genetic sequence was extracted. One or more tables may include a disease state category table 308, which may link disease states to categories of disease states; this may enable retrieval, for instance, of sets of training data elements having common categories of disease states, where categories may include any grouping of disease states, including groupings according to systems affected (e.g., endocrine versus cardiovascular or the like), disease profile categories such as auto-immune disease, inflammation-related disease, disease linked to toxicity exposures, or the like. One or more tables may include a demographic category table 312, which may link one or more elements of demographic data to a genetic sequence, permitting, for instance, retrieval of genetic training set 112 according to demographic categories such as, without limitation, ethnicity, sex, age, country of origin, location of residence, or the like. Table 1, below, lists a potential data record, as a non-limiting illustrative example, that may be retrieved from genetic record database, for instance in a query calling for genetic sequences belonging to Caucasians, and requesting the listed fields. Note that, in an embodiment, genetic sequence index may be usable to retrieve an entire genetic sequence from memory.

TABLE 1

| Genetic sequence index | Ethnicity | Age | Disease State |
|---|---|---|---|
| 102003155 | Caucasian | 52 | Hyperthyroidism |
| 102003155 | Caucasian | 52 | Liver cancer |
| 22700372 | Caucasian | 35 | Type I Diabetes |
| 80154163 | Caucasian | 67 | Rheumatoid Arthritis |

Referring again to FIG. 1, in an embodiment, computing device 104 may be configured to identify a plurality of gene combinations correlated with each disease state of a plurality of disease states identified in a plurality of pairs of genetic sequences and disease states a genetic training set 112 containing a plurality of pairs of genetic sequences and disease states using a first feature learning algorithm 120. A "feature learning algorithm," as used herein, is a machine-learning algorithm that identifies associations between elements of data in a training data set, where particular outputs and/or inputs are not specified. For instance, and without limitation, a feature learning algorithm may detect co-occurrences of gene combinations, as defined above, with each other and with disease states. Computing device 104 may perform a feature learning algorithm by dividing each genetic sequence into individual genes 208a-n, and evaluating which individual genes 208a-n and/or combinations thereof tend to co-occur with which other individual genes 208a-n and/or disease states. In an embodiment, first feature learning algorithm 120 may perform clustering of data; for instance, a number of clusters into which data from training data sets may be sorted using feature learning may be set as a number of disease states. In an embodiment, disease states may be placed in initialized clusters prior to a clustering algorithm being performed.

Still referring to FIG. 1, feature learning and/or clustering algorithm may be implemented, as a non-limiting example, using a k-means clustering algorithm. A "k-means clustering algorithm" as used in this disclosure, includes cluster analysis that partitions n observations or unclassified cluster data entries into k clusters in which each observation or unclassified cluster data entry belongs to the cluster with the nearest mean, using, for instance genetic training set 112 as described above. "Cluster analysis" as used in this disclosure, includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering whereby each observation or unclassified cluster data entry belongs to a cluster or not. Cluster analysis may include soft clustering or fuzzy clustering whereby each observation or unclassified cluster data entry belongs to each cluster to a certain degree such as for example a likelihood of belonging to a cluster; for instance, and without limitation, a fuzzy clustering algorithm may be used to identify clustering of gene combinations with multiple disease states, and vice versa. Cluster analysis may include strict partitioning clustering whereby each observation or unclassified cluster data entry belongs to exactly one cluster. Cluster analysis may include strict partitioning clustering with outliers whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering whereby observations or unclassified cluster data entries that belong to a child cluster also belong to a parent cluster.

With continued reference to FIG. 1, computing device may generate a k-means clustering algorithm receiving unclassified genetic sequence data and/or combinations as inputs and outputs a definite number of classified data entry cluster wherein the data entry clusters each contain cluster data entries. K-means algorithm may select a specific number of groups or clusters to output, identified by a variable "k." Generating a k-means clustering algorithm includes assigning inputs containing unclassified data to a "k-group" or "k-cluster" based on feature similarity. Centroids of k-groups or k-clusters may be utilized to generate classified data entry cluster. K-means clustering algorithm may select and/or be provided "k" variable by calculating k-means clustering algorithm for a range of k values and comparing results. K-means clustering algorithm may compare results across different values of k as the mean distance between cluster data entries and cluster centroid. K-means clustering algorithm may calculate mean distance to a centroid as a function of k value, and the location of where the rate of decrease starts to sharply shift, this may be utilized to select a k value. Centroids of k-groups or k-cluster include a collection of feature values which are utilized to classify data entry clusters containing cluster data entries. K-means clustering algorithm may act to classify a given disease state to one or more genetic combinations, enabling computing device 104 to identify gene combinations correlated with disease states.

With continued reference to FIG. 1, generating a k-means clustering algorithm may include generating initial estimates for k centroids which may be randomly generated or randomly selected from unclassified data input. K centroids may be utilized to define one or more clusters. K-means clustering algorithm may assign unclassified data to one or more k-centroids based on the squared Euclidean distance by first performing a data assigned step of unclassified data. K-means clustering module 108 may assign unclassified data to its nearest centroid based on the collection of centroids ci of centroids in set C. Unclassified data may be assigned to a cluster based on $argmin_{c_i \ni C} \, dist(c_i, x)^2$, where argmin includes argument of the minimum, ci includes a collection of centroids in a set C, and dist includes standard Euclidean distance. K-means clustering module 108 may then recompute centroids by taking mean of all cluster data entries assigned to a centroid's cluster. This may be calculated based on $c_i=1/|S_i|\Sigma x_i \ni S_i^{xi}$. K-means clustering algorithm may continue to repeat these calculations until a stopping criterion has been satisfied such as when cluster data entries do not change clusters, the sum of the distances have been minimized, and/or some maximum number of iterations has been reached.

Still referring to FIG. 1, k-means clustering algorithm may be configured to calculate a degree of similarity index value. A "degree of similarity index value" as used in this disclosure, includes a distance measurement indicating a measurement between each data entry cluster generated by k-means clustering algorithm and a selected combination of genes 208a-n and/or disease state. Degree of similarity index value may indicate how close a particular combination of genes 208a-n and/or disease state is to being classified by k-means algorithm to a particular cluster. K-means clustering algorithm may evaluate the distances of the combination of genes 208a-n and/or disease state to the k-number of clusters output by k-means clustering algorithm. Short distances between a combination of genes 208a-n and/or disease state and a cluster may indicate a higher degree of similarity between a combination of genes 208a-n and/or disease state and a particular cluster. Longer distances between a combination of genes 208a-n and/or disease state and a cluster may indicate a lower degree of similarity between a combination of genes 208a-n and/or disease state and a particular cluster.

With continued reference to FIG. 1, k-means clustering algorithm selects a classified data entry cluster as a function of the degree of similarity index value. In an embodiment, k-means clustering algorithm may select a classified data entry cluster with the smallest degree of similarity index value indicating a high degree of similarity between a combination of genes 208a-n and/or disease state and a particular data entry cluster. Alternatively or additionally k-means clustering algorithm may select a plurality of clusters having low degree of similarity index values to combination of genes 208a-n and/or disease state, indicative of greater degrees of similarity. Degree of similarity index values may be compared to a threshold number indicating a minimal degree of relatedness suitable for inclusion of a combination of genes 208a-n and/or disease state in a cluster, where degree of similarity indices falling under the threshold number may be included as indicative of high degrees of relatedness. The above-described illustration of feature learning using k-means clustering is included for illustrative purposes only, and should not be construed as limiting potential implementation of feature learning algorithms; persons skilled in the art, upon reviewing the entirety of this disclosure, will be aware of various additional or alternative feature learning approaches that may be used consistently with this disclosure.

With continued reference to FIG. 1, computing device may generating plurality of genotypic causal nodes 204a-n by identifying, for each disease state, one or more gene combinations associated with the disease state by a first feature learning algorithm 120; for instance, and without limitation, where first feature learning algorithm 120 is a clustering algorithm, computing device 104 may retrieve, for each disease state of the plurality of disease states, one or more gene combinations clustered with the disease state, resulting in one or more parings of disease states with gene combinations. Each such paring may be stored in a genotypic causal node 204a-n as defined above. In an embodiment, each genotypic causal node 204a-n of the plurality of genotypic causal nodes 204a-n may include an attribute, member, or data element identifying a disease state, and an attribute, member, and/or data element identifying a gene combination; the former may include at least a genotypic effect link element 228 identifying a symptomatic causal node 212a-n, for instance by matching the disease state of the genotypic causal node 204a-n with the disease state of the symptomatic causal node 212a-n.

Still referring to FIG. 1, computing device 104 is configured to generate a plurality of symptomatic nodes, each symptomatic node of the plurality of symptomatic nodes including a disease state and at least a correlated symptom. Generation of plurality of symptomatic nodes may include receiving a symptomatic training set 124 including a plurality of data entries containing a plurality of symptoms and a plurality of disease states, where a "symptomatic training set 124" may be any training data as described above. In an embodiment, each data entry of symptomatic training set 124 includes a disease state and at least a correlated symptom. Symptomatic training set 124 may be stored in and/or retrieved from a symptomatic training database 128. Symptomatic training database 128 may include any data structure suitable for use as genetic training database 116 as described above. Data entries in a symptomatic training database 128 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a symptomatic training database 128 may reflect categories, cohorts, and/or populations of data consistently with this disclosure.

Figure 4:
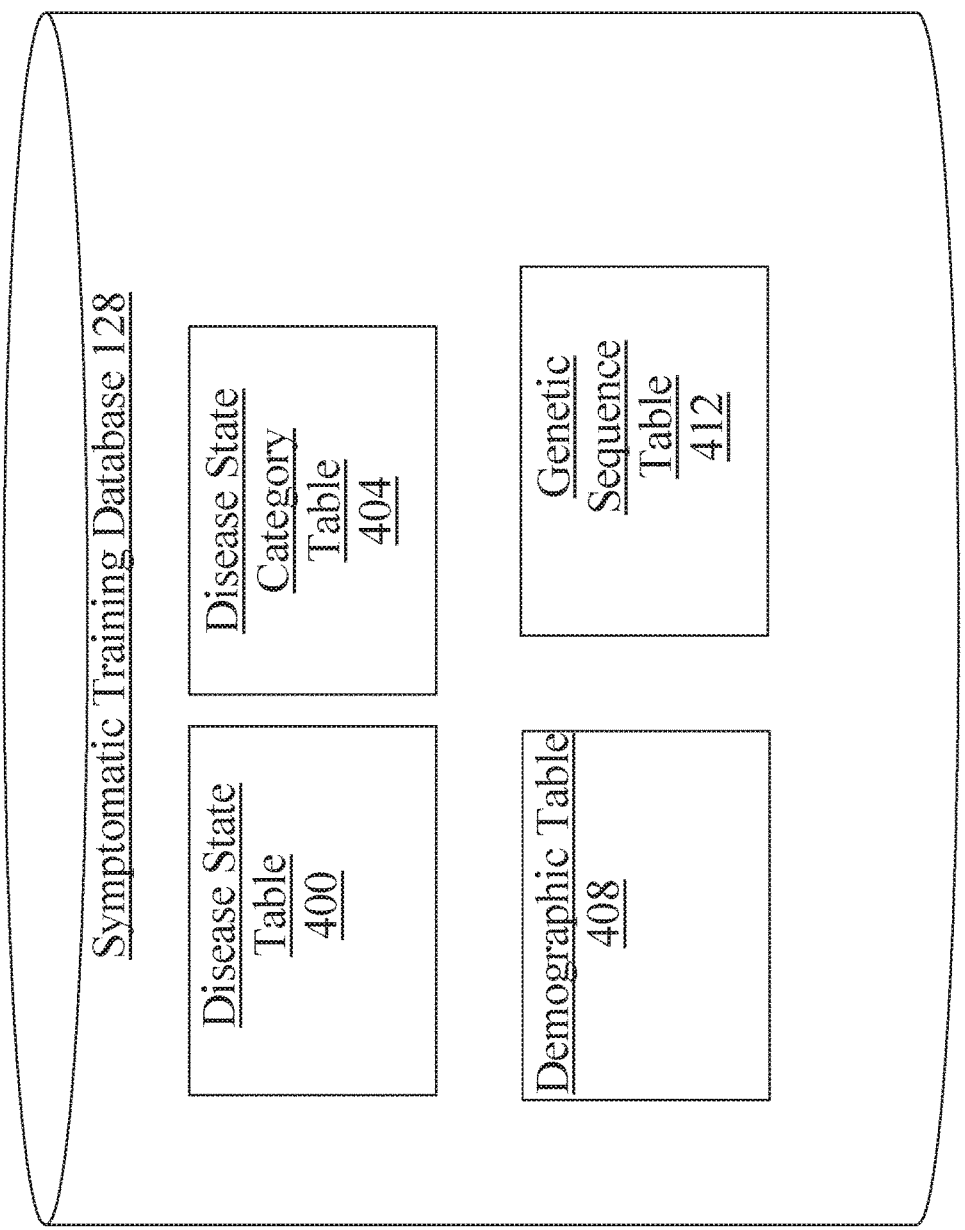
FIG. 4 is a block diagram illustrating an exemplary embodiment of a symptomatic training database.

Referring now to FIG. 4, an exemplary embodiment of a symptomatic training database 128 is illustrated. Symptomatic training database 128 may include one or more tables from which data records may be retrieved with linking data. As a non-limiting example, one or more tables may include a disease state table 400 listing one or more disease states that have been associated with a given person and/or test subject. One or more tables may include a disease state category table 404, which may link disease states to categories of disease states; this may enable retrieval, for instance, of sets of training data elements having common categories of disease states, where categories may include any grouping of disease states, including groupings according to systems affected (e.g., endocrine versus cardiovascular or the like), disease profile categories such as auto-immune disease, inflammation-related disease, disease linked to toxicity exposures, or the like. One or more tables may include a demographic category table 408, which may link one or more elements of demographic data to a record of a human subject, permitting, for instance, retrieval of symptomatic training set 124 according to demographic categories such as, without limitation, ethnicity, sex, age, country of origin, location of residence, or the like. One or more tables may include a symptom table listing symptoms reported by and/or concerning a given human subject. Table 2, below, lists a potential data record, as a non-limiting illustrative example, that may be retrieved from symptomatic training database 128, for instance in a query calling for symptomatic data regarding Caucasians, and requesting the listed fields.

TABLE 2

| Ethnicity | Age | Disease State | Symptom |
|---|---|---|---|
| Caucasian | 52 | Liver cancer | Fatigue |
| Caucasian | 52 | Liver cancer | Abdominal pain |

TABLE 2-continued

| Ethnicity | Age | Disease State | Symptom |
|---|---|---|---|
| Caucasian | 52 | Liver cancer | Indigestion |
| Caucasian | 52 | Liver cancer | Abdominal bloating |
| Caucasian | 67 | Rheumatoid Arthritis | Joint pain |

Referring again to FIG. 1, computing device may be configured to generate a plurality of symptomatic nodes using a symptomatic learning algorithm, which may include any machine-learning algorithm as described above. For instance, and without limitation, symptomatic learning algorithm may include second feature learning algorithm 132, which may include any feature learning algorithm as described above regarding generation of genotypic causal nodes 204a-n. As a non-limiting example, symptomatic learning algorithm may include a clustering algorithm such as a k-means clustering algorithm. Clustering algorithm and/or second feature learning algorithm 132 may, as a non-limiting example, instantiate clusters about disease states, where the algorithm associates one or more symptoms and/or disease states with disease states; algorithm may use fuzzy clustering, permitting a symptom to be classified to multiple disease states. In an embodiment, this multiple classification may enable results of symptomatic learning algorithm to reflect real-life scenarios, wherein, for instance, a given symptom may be consistent with a large number of possible disease conditions. Symptomatic learning algorithm may be provided with disease states that do not correspond to genetic causes, permitting one or more orphan symptomatic nodes 244 as described above; this may permit causal graph 108 to identify diagnostic situations outside the scope of analysis by causal graph 108.

With continued reference to FIG. 1, computing device 104 may generate plurality of symptomatic nodes by retrieving, for each disease state provided to symptomatic learning algorithm, one or more symptoms associated therewith by symptomatic learning algorithm; for instance, where symptomatic learning algorithm is a clustering algorithm, computing device 104 may retrieve one or more symptomatic datums 216a-n clustered with each disease state. Retrieved symptomatic datums 216a-n may be incorporated in a symptomatic node for each disease state; for instance, each symptomatic node may include a disease state and at least a correlated symptom. Symptomatic nodes may include other disease states as symptomatic data, as detected using clustering algorithms; for instance a disease state such as anemia, which in itself is associated with fatigue, syncope, pallor, and other symptoms, may in turn be a symptomatic datum that clusters to sickle cell disease, iron deficiency, hemophilia, and/or one or more internal and/or gastrointestinal bleeding disorders. In an embodiment, this may be performed by listing labeling conditions as symptomatic data in particular data entries, clustering those as separate data, so labeled, with other conditions, and then matching disease states to the symptomatic labels representing those disease states after clustering; for instance, syncope may be listed as a disease state, corresponding to a disease state cluster of its own, in medical data in which syncope was a diagnosis associated with a set of symptoms, whereas if syncope was recorded as a symptom of some other disorder, a datum with a prefix or postfix indicating a symptomatic role for syncope, which may then be clustered to other disease states. Subsequent listing of syncope as a symptomatic datum in a symptomatic node listing another disease state may then include stripping away the prefix and/or suffix; this may enable computing device 104 to add a symptomatic node for syncope downstream in directed causal graph 108 from nodes listing disease states for which syncope is a symptom.

Still referring to FIG. 1, relationships of symptoms to disease states may alternatively or additionally be detected using a prognostic label learner as described in U.S. Non-provisional patent application Ser. No. 16/354,119.

With continued reference to FIG. 1, computing device 104 is configured to generate causal graph 108 by connecting the plurality of symptomatic nodes to the plurality of genotypic nodes. Computing device 104 may instantiate edges connecting disease states of symptomatic nodes to matching disease states of genotypic nodes, as described above. Edges may include any data link or relationship directing a computing device to traverse causal graph 108 from one node to another, including pointers to data locations, indications of names and/or labels of data objects representing nodes, or the like. For instance, and without limitation, computing device 104 may generate one or more data elements of each symptomatic causal node 212a-n indicating that a genotypic causal node 204a-n and/or symptomatic causal node 212a-n lists a disease state of symptomatic causal node 212a-n, and traverse from symptomatic causal node 212a-n to genotypic causal node 204a-n and/or vice versa. As another example, computing device 104 may interpret an identification in a genotypic causal node 204a-n of a disease state as a link to a symptomatic causal node 212a-n having an identical disease state.

Still referring to FIG. 1, computing device may include one or more orphan symptomatic nodes 244 in causal graph 108; such symptomatic nodes 244, as described above, may include nodes corresponding to disease states having purely path 220ogenic and/or purely environmental causes, such as without limitation infectious diseases, poisonings, injuries, or the like. In an embodiment, such orphan nodes 244 may terminate with no higher causal node 200. This may permit computing device 104, upon traversal of causal graph 108 to such a node from a reported symptom, for instance as described below, to identifying diagnostic situations outside the scope of analysis by causal graph 108.

In an embodiment, and with further reference to FIG. 1, generation of causal graph 108 may include generation of a causal graph 108 that is specific to one or more users, categories of users, and/or cohorts of users. For instance, and without limitation, genetic training set 112 and/or symptomatic training set 124 may be assembled using entries matching one or more elements of demographic data, disease state categories, or other data categories, for instance as retrieved from genetic training database 116 and/or symptomatic training database 128 as described above. As a non-limiting, illustrative example, a causal graph 108 may be generated for cancer in African-American males living in the Midwest, while another causal graph 108 may be generated for all diseases suffered by Caucasian women of Swedish extraction, or the like. Computing device 104 may match a causal graph 108 to human subject by matching demographic and/or disease state categories, which may be stored along with graphs generated therewith, and retrieving a matching causal graph 108; alternatively or additionally, a causal graph 108 may be generated for human subject after receiving one or more elements of demographic and/or disease state data pertaining to the human subject.

In an embodiment, and with continued reference to FIG. 1, computing device 104 is configured to receive a genetic sequence of a human subject; a "genetic sequence," as used herein, is a series of genes 208a-n identified in a nucleotide sequence of chromosomal nucleic acid of a human subject, including without limitation deoxyribonucleic acid (DNA) and/or ribonucleic acid (RNA). DNA may include chromosomal DNA, including without limitation sequences encoding particular genes 208a-n as well as sequences of DNA disposed between or after gene sequences. A genetic sample may include mRNA, tRNA, or any other RNA sequence or strand. Genetic sequence may be a complete sequence of genes 208a-n of the subject and/or a subset thereof.

With continued reference to FIG. 1, genetic data may be extracted from a user by means of a physically extracted sample. Physically extracted sample may include without limitation a tissue sample, a buccal swab, a fluid sample, a chip and/or microchip embedded under the skin, a biopsy or the like. Extraction of genetic samples may be performed using any suitable physical process, including separation of nucleic acid from other tissue and/or fluid elements using, without limitation, a centrifuge. Extraction may include any form of restriction or division of a DNA and/or RNA sequence into sub-sequences, including without limitation using restriction enzymes. Extraction of genetic samples may include one or more variations of polymerase chain reaction "PCR" processes, whereby a particular strand of nucleic acid is replicated or "amplified" in a solution of nucleic acid by repeatedly exposing the solution to stimulus, such as heat, that breaks base-pair bonds, and then removing the stimulus to allow base-pair bonds to reform; as a result, a strand or sequence of nucleic acid will bond to free-floating molecules of nucleic acid, forming an inverse copy of itself, which will be separated from the strand or sequence during stimulus, and subsequently each of the strand and the inverse copy will bond to further free-floating molecules. As the above-described process is repeated, the number of copies of the strand or sequence increases exponentially. Extraction may include any suitable process to measure sequence lengths, match sequences, or the like, including without limitation electrophoresis.

Still referring to FIG. 1, received genetic sequence may be stored in any suitable manner, including without limitation in a user database 136. User database 136 may include any data structure suitable for use as genetic training database 116 as described above. Data entries in a user database 136 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a user database 136 may reflect categories of data consistently with this disclosure.

With continued reference to FIG. 1, computing device 104 is configured to receive a first symptomatic datum; first symptomatic datum may be any symptomatic datum as described above, which describes a symptom being experienced by human subject corresponding to received genetic sequence. First symptomatic datum may be received in any manner suitable for receipt of symptomatic datums 216a-n as described above, including without limitation via diagnostic tests and/or self-reported symptoms. First symptomatic data may be stored in any suitable manner, including without limitation in user database 136.

Referring now to FIG. 5, an exemplary embodiment of a user database 136 is illustrated. User database 136 may include a user genetic table 500, which may store one or more elements of user genetic sequence data. User database 136 may include a non-coding sequence table 504, which may store one or more elements of user non-coding genetic sequence data. User database 136 may include a user epigenetic table 508, which may store one or more elements of user epigenetic data. User database 136 may include a user demographic table 512, which may store one or more elements of user demographic data. User database 136 may include a user symptomatic table 516, which may store one or more elements of user symptomatic data, including any clinical test results, current and/or past diagnoses, or the like.

Referring again to FIG. 1, computing device 104 is configured to identify at least a path 220 in the causal graph 108 from inputs in the genetic sequence to outputs at the first symptomatic datum, where the at least a path 220 contains at least a genetic node and at least a linked symptomatic node. Identification of at least a path 220 may be performed as described above, including without limitation by traversal from first symptomatic datum via one or more symptomatic causal nodes 212a-n to one or more genotypic causal nodes 204a-n, which may in turn identify one or more combinations of genes 208a-n having a probable causal link to the first symptomatic datum. At least a path 220 may include a single path 220; for instance, first symptomatic datum may include a symptom or collection of symptoms singularly associated with a particular disease state, which in turn has a single genetic cause; single genetic cause may be a combination of genes 208a-n, including a combination of genes 208a-n that have not been identified by scientific study, but which are common to populations of persons having the particular disease state.

Alternatively or additionally, and still referring to FIG. 1, identification of at least a path 220 may include identifying a plurality of paths 220 in the causal graph 108 from inputs in the genetic sequence to outputs at the symptomatic datum. In an embodiment, plurality of paths 220 may be output to a medical professional or other person as described below. Alternatively or additionally, computing device 104 may be configured to select a most probable path 220 from a plurality of identified paths 220. Selecting the most probable path 220 may include receiving a second symptomatic datum and selecting the most probable path 220 using the second symptomatic datum; for instance, and without limitation, computing device may traverse causal graph 108 from second symptomatic datum via one or more symptomatic causal nodes 212a-n to one or more symptomatic causal nodes 212a-n, and select a most probable path 220 from plurality of paths 220 using the newly traversed path 220. As a non-limiting example, selecting the most probable path 220 using the second symptomatic datum may include identifying a path 220 through the graph from the genetic sequence to the second symptomatic datum and determining that the identified path 220 matches a path 220 of the plurality of paths 220. Matching, in this context, may include determining that path 220 from second symptomatic datum a node that is in a path 220, of plurality of identified paths 220, and/or that a node in path 220 from second symptomatic datum is a sibling node of a node from a path 220 of plurality of identified paths 220; in both cases, path 220 to and/or from second symptomatic datum may connect to the path 220 of the plurality of identified paths 220, as so may indicate that path 220 is likely the most probable path 220 of the plurality of identified paths 220. A symptomatic node in the path 220 from second symptomatic datum may be a sibling node of a node in the identified path 220 where the symptomatic sibling node contains a cause link element 232 matching a causal node 200 in a path 220 of the plurality of paths 220. For instance, computing device may identify a symptomatic sibling node of plurality of symptomatic causal nodes 212a-n where symptomatic sibling node contains a genotypic effect link element 228 matching a genotypic effect link element 228 linked to the second symptomatic datum. Path 220 from second symptomatic datum may be included with selected path 220 of plurality of paths 220 in a genetic causal model as described in further detail below.

Alternatively or additionally, and continuing to refer to FIG. 1, selecting the most probable path 220 using the second symptomatic datum may include determining that the second symptomatic datum contradicts a causal node 200 of a path 220 of the plurality of paths 220 and eliminating the path 220. For instance, second symptomatic datum may indicate a disease state that is mutually exclusive of a disease state represented by a symptomatic causal node 212*a-n* in graph; computing device 104 may determine as a result that a path 220 of the plurality of identified paths 220 that contains the symptomatic causal node 212*a-n* that is mutually exclusive should be eliminated. Alternatively or additionally, one or more experts may input data, using any method suitable for input of expert data as described for instance in U.S. Nonprovisional patent application Ser. No. 16/354,119, listing one or more elements of symptomatic data that eliminates a given disease state as a likely diagnosis; such expert entries may be included in symptomatic causal nodes 212*a-n* and/or in a table listing disease states, and used by computing device 104 to eliminate paths 220 containing symptomatic causal nodes 212*a-n* associated with the expert entries upon entry of second symptomatic datum matching such expert entries.

Still referring to FIG. 1, selecting a most probable path 220 from a plurality of paths 220 may include determining that a gene in a combination of genes 208*a-n* in a path 220 of the plurality of paths 220 is not being expressed. A combination of genes 208*a-n* is "in a path 220," as used herein, where the combination of genes 208*a-n* is identified and/or linked to in a genetic node that is part of the path 220. In an embodiment, whether a particular gene is being expressed may depend on factors beyond genetic data itself, including non-coding genetic sequences, epigenetic data such as methylation, or the like. A non-coding genetic sequence, as used herein, is a sequence of nucleic acid such as DNA that does not encode a gene; i.e., the non-coding sequence is not a part of the code for an amino acid sequence to be converted into a protein. Some non-coding sequences of nucleic acid such as DNA may affect expression of a gene; for instance, a non-coding section of DNA may determine where a transcription factor, defined as a protein that binds to non-coding DNA sequences and controls how a gene is regulated, may attach. A transcription factor may attach to a "promoter" sequence near a gene and increase or decrease a rate of transcription of the gene. A non-coding genetic sequence may include an "operator," defined as a sequence to which a "repressor" protein binds, preventing expression of the gene. A non-coding genetic sequence may include an "enhancer," where proteins may attach to increase a rate of expression of a gene. A non-coding genetic sequence may include a "silencer," which stops transcription of a gene when bound by a particular kind of protein. Non-coding sequences may include one or more elements of genetic data that disrupt one of the above-described gene-regulating non-coding sequences, including without limitation sequences introduced in transcription errors, sequences introduced by viruses, transposons, or other sequence-modifying elements, or the like.

In an embodiment, and still referring to FIG. 1, computing device 104 may receive a non-coding training set 140 correlating genes 208*a-n* and non-coding sequences to gene expression data, where gene expression may be determined using any suitable process, including without limitation using proteomic analysis to detect whether a given protein coded by a gene is being expressed or not. Non-coding training set 140 may have any form suitable for use as training data as described above. Computing device 104 may be configured to generate a non-coding classifier 144. Non-coding classifier 144 may include a classifier, as defined above, that takes a combination of a gene and non-coding genetic sequence data as inputs and generates an output classifying the gene to expressed or non-expressed statuses, indicating respectively that the gene is being expressed or that the gene is not being expressed. Computing device 104 may be configured to determine whether the gene is being expressed by inputting the gene and non-coding genetic data of human subject to the non-coding classifier 144, receiving an output from the non-coding classifier 144, and determining based on the output that the gene is being expressed or that the gene is not being expressed. In an embodiment, where computing device 104 determines that a gene is not being expressed, computing device may eliminate a path 220 containing the gene. Alternatively or additionally, non-coding classifier 144 may generate a non-binary classification output, such as a classification output classifying a gene as not expressed, expressed at a low rate, expressed at a medium rate, or expressed at a high rate, as determined by degrees of expression regulated by non-coding genetic data. These outputs may include weights, such as integers to be multiplied by a probability that given path 220 is a most probable path 220; such weights may be referred to herein as a "non-coding probability factor."

With continued reference to FIG. 1, computing device 104 may use any classification algorithm to generate non-coding classifier 144, including without limitation linear classifiers such as logistic regression classifiers, naïve Bayes classifiers, support vector machines, decision trees, boosted trees, random-forest classifiers, and/or neural networks. Classification algorithm may include, without limitation, a K-nearest neighbors algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using Euclidean distance measurement. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values. As a non-limiting example, K-nearest neighbors algorithm may be configured to classify an input vector including a gene and one or more elements of non-coding genetic sequence data to expressed and non-expressed clusters; alternatively or additionally, k-nearest neighbors may classify input vector by vector similarity to a cluster of a non-binary set of clusters, such as clusters classifying a gene as not expressed, expressed at a low rate, expressed at a medium rate, or expressed at a high rate, as determined by degrees of expression regulated by non-coding genetic data. Classifications may generate non-coding probability factors as described above.

Still referring to FIG. 1, computing device 104 may be configured to select a most probable path 220 of a plurality of paths 220 using epigenetic data. Epigenetic data may include data describing epigenetic effects that influence gene expression. For instance, where DNA code for a gene includes a gene promoter, or sequence of DNA that leads to initiation of transcription of the gene, a methyl group added at the gene promoter may suppress expression of that gene. Methylation may be detected by introducing restriction enzymes that cleave DNA at methylated loci, and examination of a resulting DNA assay, which may be performed, without limitation, using any genetic extraction and/or measurement process as described above.

In an embodiment, and continuing to refer to FIG. 1, computing device 104 may receive a epigenetic training set 148 112 correlating genes 208a-n and epigenetic data to gene expression data, where gene expression may be determined using any suitable process, including without limitation using proteomic analysis to detect whether a given protein coded by a gene is being expressed or not. Epigenetic training set 148 112 may have any form suitable for use as training data as described above. Computing device 104 may be configured to generate an epigenetic classifier 152. Epigenetic classifier 152 may include any classifier suitable for use as non-coding classifier 144, that takes a combination of a gene and epigenetic data as inputs and generates an output classifying the gene to expressed or non-expressed statuses, indicating respectively that the gene is being expressed or that the gene is not being expressed. Computing device 104 may be configured to determine whether the gene is being expressed by inputting the gene and epigenetic data of human subject to the epigenetic classifier 152, receiving an output from the epigenetic classifier 152, and determining based on the output that the gene is being expressed or that the gene is not being expressed. In an embodiment, where computing device 104 determines that a gene is not being expressed, computing device may eliminate a path 220 containing the gene. Alternatively or additionally, epigenetic classifier 152 may generate a non-binary classification output, such as a classification output classifying a gene as not expressed, expressed at a low rate, expressed at a medium rate, or expressed at a high rate, as determined by degrees of expression regulated by non-coding genetic data. These outputs may include weights, such as integers to be multiplied by a probability that given path 220 is a most probable path 220; such weights may be referred to herein as a "epigenetic probability factor."

In an embodiment, and still referring to FIG. 1, computing device 104 may be configured to use protein expression traits, which may include proteomic data, or other data used to detect gene expression directly, to determine whether a gene is being expressed in a human subject. Such data may include, without limitation, detection of RNA such as mRNA and/or tRNA matching a gene, detection of one or more proteins that are produce using the gene, and/or detection of one or more additional phenotypical data indicating that the gene is expressed. Computing device 104 may, as a non-limiting example, receive a gene expression training set 156 correlating genes 208a-n and protein expression traits, to gene expression data, where gene expression may be determined using any suitable process, including without limitation using proteomic analysis to detect whether a given protein coded by a gene is being expressed or not. Gene expression training set 156 may have any form suitable for use as training data as described above. Computing device 104 may be configured to generate a gene expression classifier 160. Gene express classifier may include any classifier suitable for use as non-coding classifier 144 as described above, that takes a combination of a gene and protein expression trait data as inputs and generates an output classifying the gene to expressed or non-expressed statuses, indicating respectively that the gene is being expressed or that the gene is not being expressed. Computing device 104 may be configured to determine whether the gene is being expressed by inputting the gene and protein expression trait data of human subject to the gene expression classifier 160, receiving an output from the gene expression classifier 160, and determining based on the output that the gene is being expressed or that the gene is not being expressed. In an embodiment, where computing device 104 determines that a gene is not being expressed, computing device may eliminate a path 220 containing the gene. Alternatively or additionally, gene expression classifier 160 may generate a non-binary classification output, such as a classification output classifying a gene as not expressed, expressed at a low rate, expressed at a medium rate, or expressed at a high rate, as determined by degrees of expression regulated by protein expression trait data. These outputs may include weights, such as integers to be multiplied by a probability that given path 220 is a most probable path 220; such weights may be referred to herein as a "gene expression probability factor."

With continued reference to FIG. 1, computing device 104 may be configured to select a most probable path 220 of a plurality of causal paths 220 by determining whether a first gene combination suppresses expression of a second gene combination, where "suppressing," in this context, indicates that presence of the first gene combination correlates to a lack of expression and/or reduced expression of the second gene combination. Computing device 104 may receive a co-expression training set 164 correlating pairs of gene combinations and co-expression sequences to gene expression data, where gene expression may be determined using any suitable process, including without limitation using proteomic analysis to detect whether a given protein coded by a gene is being expressed or not. Co-expression training set 164 may have any form suitable for use as training data as described above. Computing device 104 may be configured to generate a co-expression classifier 168. Co-expression classifier 168 may include a classifier, as defined above, that takes a pair of gene combinations as inputs and generates an output classifying each gene of the pair of gene combinations to expressed or non-expressed statuses, indicating respectively that each gene combination is being expressed or is not being expressed. Computing device 104 may be configured to determine whether a gene combination is being expressed by inputting the gene combination and one or more other elements of genetic data of human subject to the co-expression classifier 168, receiving an output from the co-expression classifier 168, and determining based on the output that the gene combination is being expressed or that the gene combination is not being expressed. In an embodiment, where computing device 104 determines that a gene combination is not being expressed, computing device may eliminate a path 220 containing the gene. Alternatively or additionally, co-expression classifier 168 may generate a non-binary classification output, such as a classification output classifying a gene combination as not expressed, expressed at a low rate, expressed at a medium rate, or expressed at a high rate, as determined by degrees of expression regulated by one or more other genes 208a-n and/or gene combinations. These outputs may include weights, such as integers to be multiplied by a probability that given path 220 is a most probable path 220; such weights may be referred to herein as a "co-expression probability factor."

Still referring to FIG. 1, computing device 104 may be configured to perform alternate cause analysis, defined for the purposes of this disclosure as detection of one or more potential non-genetic causes for symptomatic datums 216a-n and/or disease states as represented in symptomatic causal nodes 212a-n. Such non-genetic causes may include infectious agents, environmental causes such as toxins and/or radiation exposure, injury, or the like. Alternate cause analysis may be useful, for instance, where a non-genetic cause may produce similar symptoms to a genetic condition. For instance, and without limitation, chronic traumatic encephalopath 220y (CTE), induced by repeated physical shocks to the central nervous system, may produce symptoms consistent with dementia, depression, and/or neuromuscular disorders such as amyotrophic lateral sclerosis (ALS); inclusion in symptomatic training set 124 of elements including such causes may result in generation of orphan nodes 224 that indicate a non-genetic cause. Similarly, certain chronic infections such as Lyme's disease, Chagas, and the measles virus may create symptoms such as neurological degeneration, arthritis, heart failure, or the like that may be easily confused with genetic causes; inclusion in symptomatic training set 124 of elements including such causes may result in generation of orphan nodes 224 that indicate a non-genetic cause. Environmental exposure to toxins and/or radiation can also cause symptoms that may be confused with genetic disorders; for instance, increasingly confused cognition, depression, and impulsive behavior may be consistent with various heritable mental disorders but may also be consistent with mercury poisoning. Inclusion in symptomatic training set 124 of elements including such causes may result in generation of orphan nodes 224 that indicate a non-genetic cause. Computing device 104 may be configured to aggregate probabilities of such orphan nodes 224 in causal graph 108 as selected by methods described above to determine an "alternate cause factor," which may be used to weight one or more paths 220 of plurality of paths 220.

Continuing to refer to FIG. 1, computing device 104 may determine a probability of correctness of each path 220 of a plurality of paths 220 in causal graph 108. Symptomatic learning algorithm and/or genetic learning algorithm, as described above, may generate probabilities of each connection between nodes; for instance, a degree of probability that a disease state represented in symptomatic node is a cause of a symptom represented by first symptomatic datum and/or second symptomatic datum may be generated by symptomatic learning algorithm and included as a weight in a corresponding symptomatic causal node 212a-n and/or associated therewith by computing device 104. As a further non-limiting example, a degree of probability that a gene combination represented in a genotypic causal node 204a-n is a cause of a disease state represented by that genetic causal node 200 may be generated by genetic learning algorithm and included as a weight in a corresponding genotypic causal node 204a-n and/or associated therewith by computing device 104. Probabilities for each causal node 200 in a path 220 through causal graph 108 may be aggregated according to any statistically sound method for combinations of probabilities to generate a probability for each path 220 of plurality of paths 220. Alternatively or additionally, each path 220 may have probability initialized to an equal fraction of 1 with each other identified path 220. In either case, probabilities associated with each path 220 may be multiplied by one or more factors as described above, including a non-coding probability factor, a gene expression probability factor, an epigenetic probability factor, and/or an alternate cause factor. Probabilities associated with each path 220 may be multiplied by additional factors, such as a path 220 multiplicity factor which reduces each path 220's probability in proportion to a number of total paths 220, or the like. Probabilities may be used after multiplication to rank paths 220 by relative probability; ranking may be presented to users and/or used to eliminate lower-ranked paths 220, for instance where lower-ranked paths 220 fall below a threshold probability level. The above methods may be combined; for instance, paths 220 may be eliminated according to any process for elimination of paths 220 as described above, and multiplication by factors may occur before or after elimination.

Still referring to FIG. 1, computing device may be configured to generate a causal model using the at least a genetic node and the at least a linked symptomatic node. Generation of causal model may include storage in memory of selected causal path 220 or paths 220. Generation of causal model may include generation of a report, document, and/or display in a graphical user interface describing one or more possible disease states and genetic causes as represented by nodes in selected path 220 or paths 220; descriptions may be generated using narrative language, image, or similar processes for generation of narrative language as described in U.S. Nonprovisional patent application Ser. No. 16/354,119. In an embodiment, where a selected path 220 includes an orphan symptomatic node 244 as described above, a message or report indicating that disease state and/or symptom is likely not genetic in origin may be generated.

With continued reference to FIG. 1, causal model may be displayed, printed, and/or otherwise provided to a user such as a doctor or other provider of medical treatment. In an embodiment, computing device 104 may be configured to receive, from a user, an input modifying causal model. For instance, a doctor or other user may enter an input indicating that a given path 220 of at least a path 220 in causal graph 108 is not a cause of one or more symptomatic data; computing device 104 may eliminate the path 220 from causal model, and/or may repeat one or more steps as described above, such as without limitation recalculating probabilities for a plurality of paths 220 in causal graph 108 excluding the path 220 eliminated by instruction, determining a new most probable path 220 and/or a ranking of most probable paths 220, regenerating causal model, and/or providing a regenerated and/or modified causal model to a user. A user may alternatively or additionally enter one or more second symptomatic datums 216*a-n* as described above to eliminate one or more paths 220 and/or to determine that one or more paths 220 are more probable; a second symptomatic datum may be generated using any clinical testing method as described above.

Figure 6:
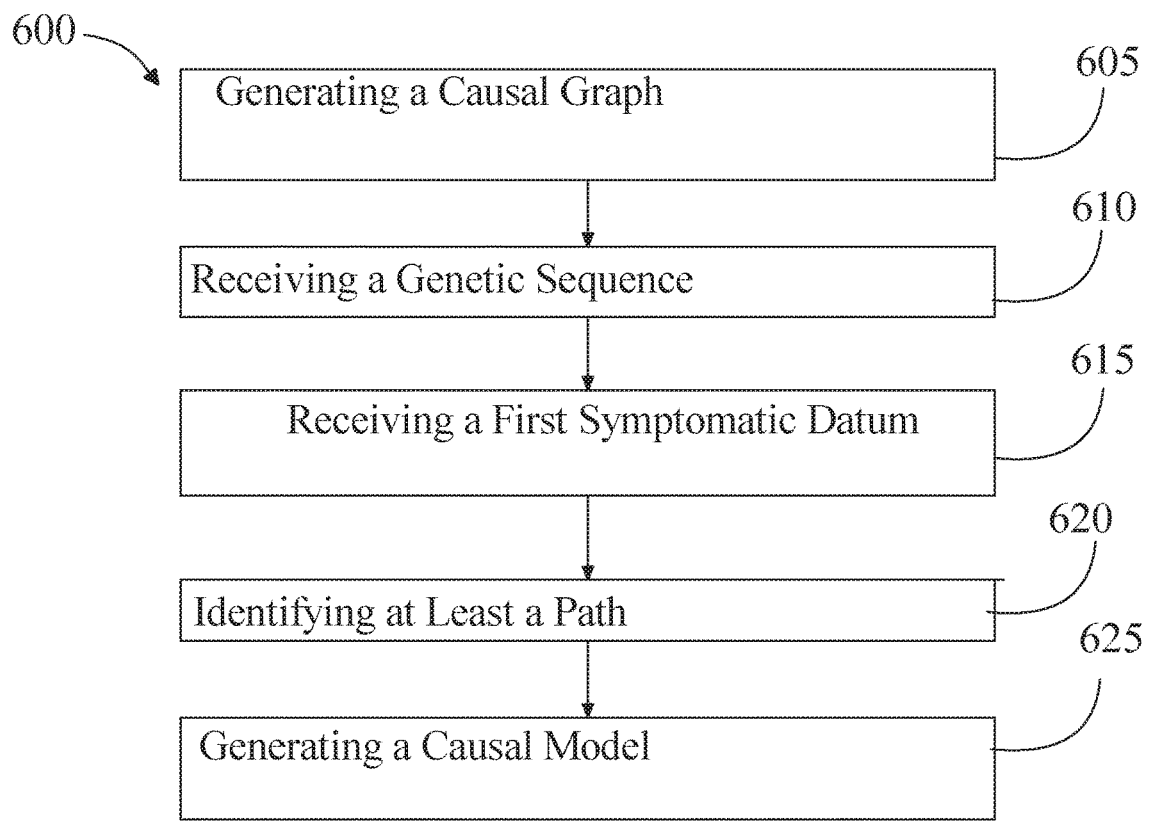
FIG. 6 is flow diagram representing an exemplary embodiment of a method of generating a genotypic causal model of a disease state.

Referring now to FIG. 6, an exemplary embodiment of a method 600 of generating a genotypic causal model of a disease state is illustrated. At step 605, a computing device 104 generates a causal graph 108 containing a plurality of causal nodes 200, the plurality of causal nodes 200 including a plurality of genotypic causal nodes 204*a-n* and a plurality of symptomatic causal nodes 212*a-n*. This may be performed, without limitation, as described above in reference to FIGS. 1-5.

Figure 7:
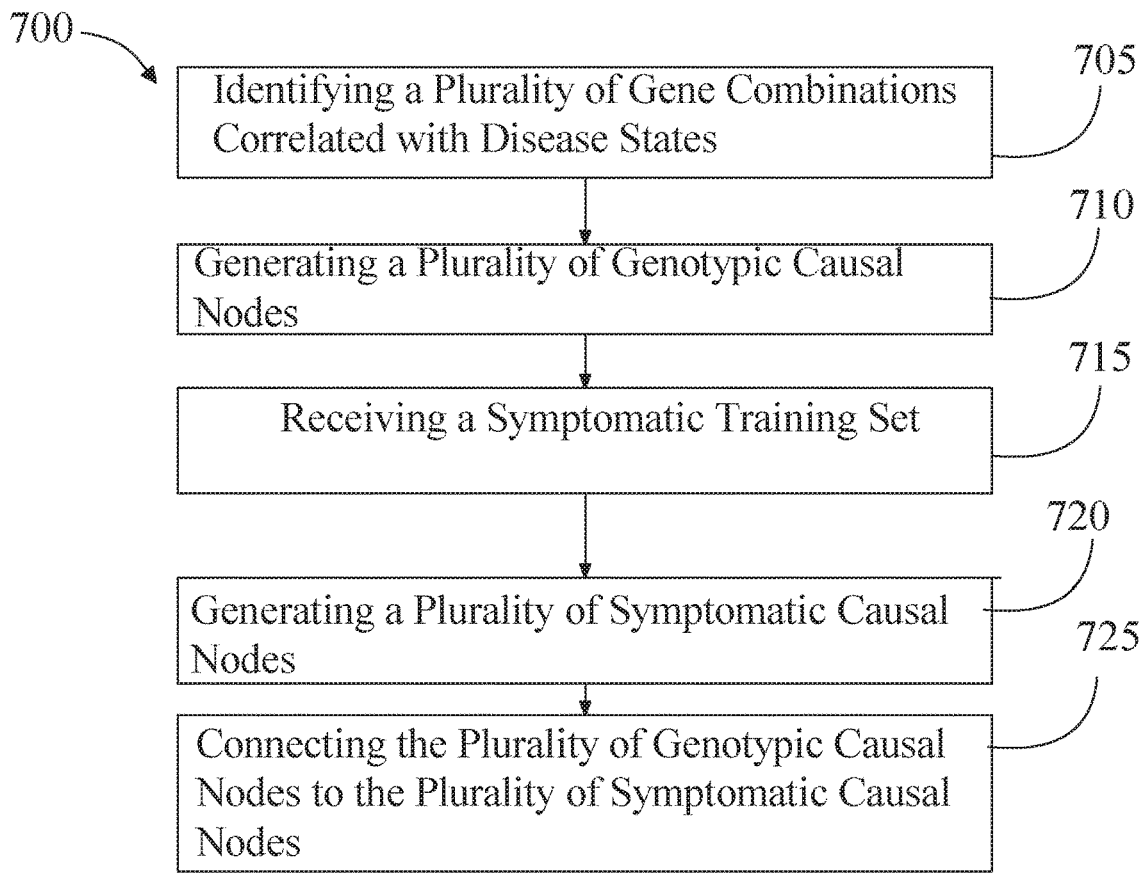
FIG. 7 is a flow diagram illustrating an exemplary embodiment of method steps for generating a causal graph.

Referring now to FIG. 7, exemplary embodiments of steps that may be performed to generate causal graph 108 are illustrated. At step 705, generation may include identifying, using a first feature learning algorithm 120, in training data containing a plurality of pairs of genetic sequences and disease states, a plurality of gene combinations correlated with each disease state of a plurality of disease states identified in the plurality of pairs; this may be implemented, without limitation, as described above in reference to FIGS. 1-5. At step 710, plurality of genotypic causal nodes 204*a-n* may eb be generated, wherein each genotypic causal node 204*a-n* includes a disease state and a gene combination correlated with the disease state; this may be implemented, without limitation, as described above in reference to FIGS. 1-5. At step 715, a symptomatic training set 124 including a plurality of data entries containing a plurality of symptoms and a plurality of disease states may be received, where each data entry includes a disease state and at least a correlated symptom; this may be implemented, without limitation, as described above in reference to FIGS. 1-5. At step 720, generating, a plurality of symptomatic nodes may be generated using a second feature learning algorithm 132, where each symptomatic node includes a disease state and at least a correlated symptom; this may be implemented, without limitation, as described above in reference to FIGS. 1-5. At step 725, plurality of symptomatic nodes may be connected to plurality of genotypic nodes by instantiating edges connecting disease states of symptomatic nodes to matching disease states of genotypic nodes; this may be implemented, without limitation, as described above in reference to FIGS. 1-5.

Referring again to FIG. 6, at step 610, computing device 104 receives a genetic sequence, where the genetic sequence further comprises a series of genes 208*a-n* identified in a nucleotide sequence of chromosomal nucleic acid of a human subject; this may be implemented, without limitation, as described above in reference to FIGS. 1-5. At step 615, computing device 104 receives a first symptomatic datum; this may be implemented, without limitation, as described above in reference to FIGS. 1-5. At step 620, computing device identifies at least a path 220 in the causal graph 108 from inputs in the genetic sequence to outputs at the first symptomatic datum, wherein the at least a path 220 contains at least a genetic node and at least a linked symptomatic node; this may be implemented, without limitation, as described above in reference to FIGS. 1-5. At step 625, computing device generates a causal model using the at least a genetic node and the at least a linked symptomatic node; this may be implemented, without limitation, as described above in reference to FIGS. 1-5.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
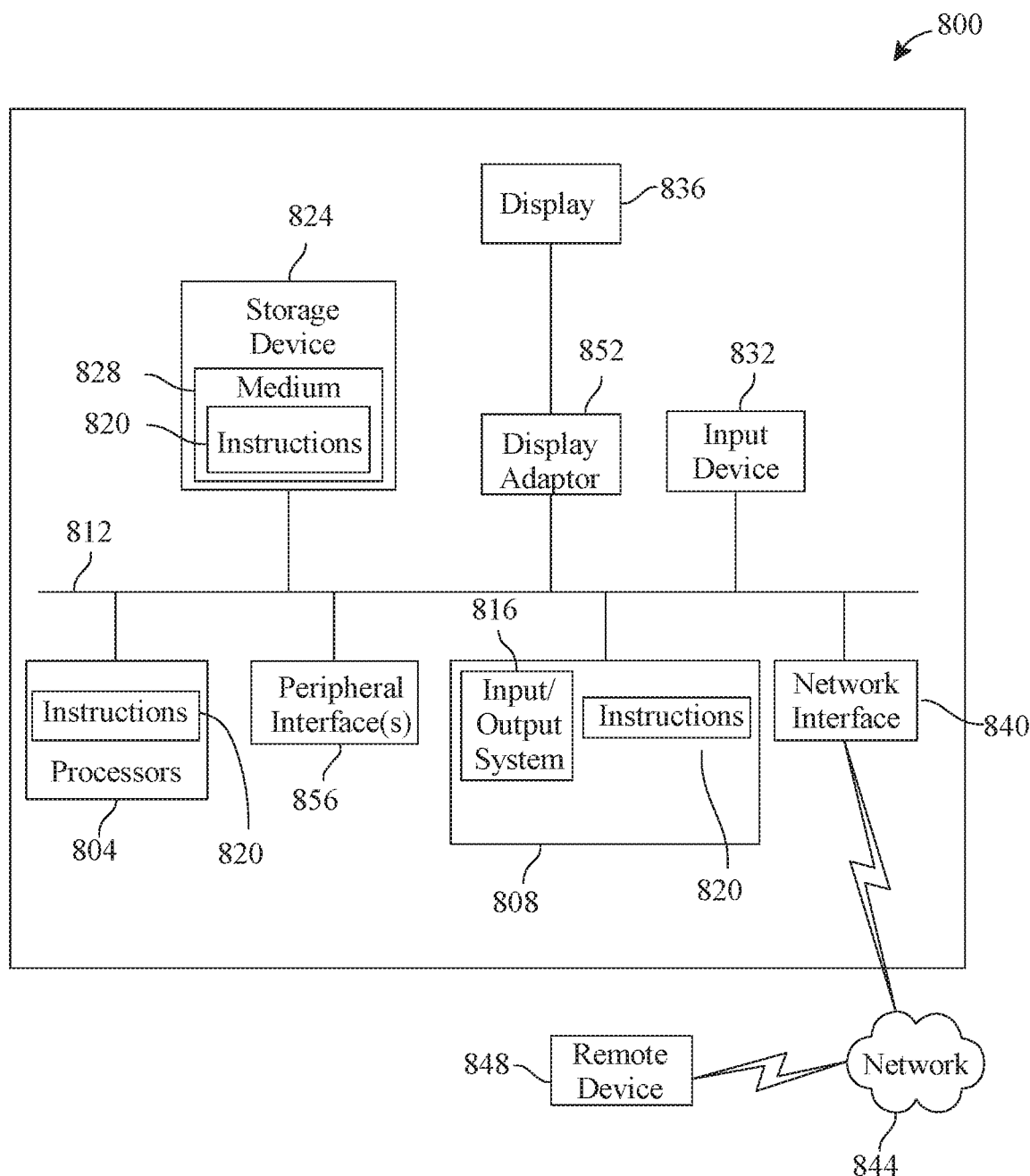
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Memory 808 may include various components (e.g., machine-readable media) including, but not limited to, a random access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIRE-WIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve embodiments described in this disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a genotypic causal model of a disease state, the system comprising a computing device configured to perform the steps of:
   generating a machine-learning model including a causal graph containing a plurality of causal nodes comprising a plurality of genotypic causal nodes and a plurality of symptomatic causal nodes, wherein generating the machine learning model further comprises:
      generating using a first feature learning algorithm, the plurality of genotypic causal nodes, wherein each genotypic causal node includes a disease state and a gene combination correlated with the disease state, wherein generating the plurality of genotypic causal nodes comprises identifying, using the first feature learning algorithm, in genetic training set data, a plurality of pairs of genetic sequences and disease states, and outputting a plurality of gene combinations correlated with each disease state of a plurality of disease states identified in the plurality of pairs, said first feature learning algorithm comprising a neural network configured to identify associations within the genetic training data;
      generating, using a second feature learning algorithm comprising a neural network, the plurality of symptomatic nodes, wherein each symptomatic node includes a disease state and at least a correlated symptom and wherein generating the plurality of symptomatic nodes comprises receiving a symptomatic training set including a plurality of data entries containing a plurality of symptoms and a plurality of disease states, wherein each data entry includes a disease state and at least a correlated symptom; and
      connecting the plurality of symptomatic nodes to the plurality of genotypic nodes by instantiating edges connecting disease states of symptomatic nodes to matching disease states of genotypic nodes;
   receiving a genetic sequence comprising a series of genes identified in a nucleotide sequence of chromosomal nucleic acid of a human subject and a first symptomatic datum as inputs;
   outputting at least a path in the causal graph from inputs in the genetic sequence to outputs at the first symptomatic datum, wherein the at least a path contains at least a genotypic node and at least a linked symptomatic node; and
   generating a causal model, as a function of the at least a path in the causal graph including the at least a genotypic node and the at least a linked symptomatic node, wherein the causal model comprises a data structure describing disease states and genetic causes.

2. The system of claim 1, wherein the first feature learning algorithm further comprises a k-means clustering algorithm.

3. The system of claim 1, wherein each symptomatic causal node includes a plurality of cause link elements, each cause link element of the plurality of cause link elements identifying a causal node of the plurality of causal nodes.

4. The system of claim 1, wherein outputting the at least a path further comprises:
   identifying a plurality of paths in the causal graph from inputs in the genetic sequence to outputs at the symptomatic datum; and
   selecting a most probable path from the plurality of paths.

5. The system of claim 4, wherein selecting the most probable path further comprises:
   receiving a second symptomatic datum; and
   selecting the most probable path using the second symptomatic datum.

6. The system of claim 5, wherein selecting the most probable path using the second symptomatic datum further comprises:
   identifying a path through the graph from the genetic sequence to the second symptomatic datum; and
   determining that the identified path matches a path of the plurality of paths.

7. The system of claim 6, wherein determining that the identified path matches a path of the plurality of paths further comprises:
   identifying a symptomatic sibling node in the identified path, wherein the symptomatic sibling node contains a cause link element matching a causal node in a path of the plurality of paths.

8. The system of claim 5, wherein selecting the most probable path using the second symptomatic datum further comprises:
   determining that the second symptomatic datum contradicts a causal node of a path of the plurality of paths; and
   eliminating the path.

9. The system of claim 1, wherein generating the plurality of symptomatic nodes further comprises generating, by the second feature learning algorithm, a plurality of clusters, each of the plurality of clusters comprising a symptom associated with one or more disease states, said second feature learning algorithm including a fuzzy logic algorithm.

10. A method of generating a genotypic causal model of a disease state, the method comprising:
   generating, by a computing device, a machine-learning model including a causal graph containing a plurality of causal nodes comprising a plurality of genotypic causal nodes and a plurality of symptomatic causal nodes, wherein generating the machine learning model further comprises:
      generating, using a first feature learning algorithm, the plurality of genotypic causal nodes, wherein each genotypic causal node includes a disease state and a gene combination correlated with the disease state, wherein generating the plurality of genotypic causal nodes comprises identifying, using the first feature learning algorithm, in genetic training set data, a plurality of pairs of genetic sequences and disease states, and outputting a plurality of gene combinations correlated with each disease state of a plurality of disease states identified in the plurality of pairs, said first feature learning algorithm comprising a neural network configured to identify associations within the genetic training data;

generating, using a second feature learning algorithm comprising a neural network, the plurality of symptomatic nodes, wherein each symptomatic node includes a disease state and at least a correlated symptom and wherein generating the plurality of symptomatic nodes comprises receiving a symptomatic training set including a plurality of data entries containing a plurality of symptoms and a plurality of disease states, wherein each data entry includes a disease state and at least a correlated symptom; and connecting the plurality of symptomatic nodes to the plurality of genotypic nodes by instantiating edges connecting disease states of symptomatic nodes to matching disease states of genotypic nodes;

receiving a genetic sequence comprising a series of genes identified in a nucleotide sequence of chromosomal nucleic acid of a human subject and a first symptomatic datum as inputs;

outputting at least a path in the causal graph from inputs in the genetic sequence to outputs at the first symptomatic datum, wherein the at least a path contains at least a genotypic node and at least a linked symptomatic node; and generating a causal model, as a function of the at least a path in the causal graph including the at least a genotypic node and the at least a linked symptomatic node, wherein the causal model comprises a data structure describing disease states and genetic causes.

11. The method of claim 10, wherein the first feature learning algorithm further comprises a k-means clustering algorithm.

12. The method of claim 10, wherein each symptomatic causal node includes a plurality of cause link elements, each cause link element of the plurality of cause link elements identifying a causal node of the plurality of causal nodes.

13. The method of claim 10, wherein outputting the at least a path further comprises:
identifying a plurality of paths in the causal graph from inputs in the genetic sequence to outputs at the symptomatic datum; and
selecting a most probable path from the plurality of paths.

14. The method of claim 13, wherein selecting the most probable path further comprises:
receiving a second symptomatic datum; and
selecting the most probable path using the second symptomatic datum.

15. The method of claim 14, wherein selecting the most probable path using the second symptomatic datum further comprises:
identifying a path through the graph from the genetic sequence to the second symptomatic datum; and
determining that the identified path matches a path of the plurality of paths.

16. The method of claim 15, wherein determining that the identified path matches a path of the plurality of paths further comprises:
identifying a symptomatic sibling node in the identified path, wherein the symptomatic sibling node contains a cause link element matching a causal node in a path of the plurality of paths.

17. The method of claim 14, wherein selecting the most probable path using the second symptomatic datum further comprises:
determining that the second symptomatic datum contradicts a causal node of a path of the plurality of paths; and
eliminating the path.

18. The method of claim 10, wherein generating the plurality of symptomatic nodes further comprises generating, by the second feature learning algorithm, a plurality of clusters, each of the plurality of clusters comprising a symptom associated with one or more disease states, said second feature learning algorithm including a fuzzy logic algorithm.

* * * * *